United States Patent
Roe et al.

(10) Patent No.: US 11,239,698 B1
(45) Date of Patent: Feb. 1, 2022

(54) DIGITALLY TIMED CMOS RECTIFIER FOR WIRELESS POWER TRANSFER

(71) Applicant: Medtronic, Inc., Minneapolis, MN (US)

(72) Inventors: Jacob A. Roe, North St. Paul, MN (US); Joel B. Artmann, Elk River, MN (US); Jonathan P. Roberts, Coon Rapids, MN (US); David J. Peichel, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/087,685

(22) Filed: Nov. 3, 2020

(51) Int. Cl.
*H02J 50/10* (2016.01)
*H02J 50/80* (2016.01)
*H02M 7/219* (2006.01)
*A61M 60/871* (2021.01)
*A61M 60/148* (2021.01)

(52) U.S. Cl.
CPC .......... *H02J 50/10* (2016.02); *A61M 60/871* (2021.01); *H02J 50/80* (2016.02); *H02M 7/219* (2013.01); *A61M 60/148* (2021.01); *A61M 2205/8243* (2013.01)

(58) Field of Classification Search
CPC .............. A61M 60/148; A61M 60/871; A61M 2205/8243; H02J 50/10; H02J 50/80; H02M 7/219
USPC ........................................................ 307/104
See application file for complete search history.

(56) References Cited

U.S. PATENT DOCUMENTS

| 8,472,221 B1 | 6/2013 | Lee | |
| 10,256,661 B1* | 4/2019 | Lu | H02J 7/342 |
| 10,333,296 B1* | 6/2019 | Wu | A61B 34/30 |
| 11,025,081 B2* | 6/2021 | Wu | H02J 7/025 |
| 2011/0124310 A1 | 5/2011 | Theilmann et al. | |
| 2013/0235635 A1 | 9/2013 | Takahagi et al. | |

(Continued)

FOREIGN PATENT DOCUMENTS

EP        0976420 A1    2/2000

OTHER PUBLICATIONS

International Rectifier, www.irf.com, Mar. 26, 2013, 20 pages.
International Search Report and Written Opinion of International Application No. PCT/US2021/051437, dated Dec. 21, 2021, 15 pp.

*Primary Examiner* — William Hernandez
(74) *Attorney, Agent, or Firm* — Shumaker & Sieffert, P.A.

(57) ABSTRACT

A digitally timed complementary metal oxide semiconductor (CMOS) rectifier for wireless power transfer in an implanted medical device is provided. According to one aspect, a voltage rectification circuit for a medical device having an internal coil and internal circuitry includes a voltage rectifier comprising a complementary metal oxide semiconductor (CMOS) circuit having low-side first type MOS transistors and upper cross-coupled second type MOS transistors. The voltage rectifier may be configured to output a rectified received voltage, each low-side first type MOS transistor being configured with an first type MOS body diode, the low-side first type MOS transistors being enabled by a timing signal to provide conduction through the low-side first type MOS transistors while bypassing conduction through the first type MOS body diode during a time window having a duration determined by voltage level crossings of the received voltage.

20 Claims, 8 Drawing Sheets

(56) References Cited

U.S. PATENT DOCUMENTS

| | | | |
|---|---|---|---|
| 2015/0042274 A1* | 2/2015 | Kim | H02J 7/06 320/108 |
| 2017/0288568 A1 | 10/2017 | Grasso et al. | |
| 2019/0356151 A1 | 11/2019 | Wu et al. | |
| 2020/0195164 A1 | 6/2020 | Zhan et al. | |

* cited by examiner

DIGITALLY TIMED CMOS RECTIFIER FOR WIRELESS POWER TRANSFER

CROSS-REFERENCE TO RELATED APPLICATION n/a.

FIELD

The present technology is generally related to implantable medical devices such as a left ventricular assist device (LVAD), and more particularly to a digitally timed complementary metal oxide semiconductor (CMOS) rectifier for wireless power transfer in an implanted medical device.

BACKGROUND

Referring to FIG. 1, an implantable LVAD system 10 has internal components (in the body of the patient) and external components. The LVAD system 10 may typically include an LVAD pump 12 an implanted controller (i-controller) 14 having an internal battery 16, an implanted internal transcutaneous energy transfer system (TETS) coil (i-coil) 18, an external TETS coil (e-coil) 20 and an external power transmitter 21 with a detachable battery 24. In operation, power is supplied from the external power transmitter 21 to the i-controller 14 via mutual coupling of the coils 18 and 20, in order to charge the internal battery 16 of the i-controller 14 and to power the LVAD pump 12. The coils 18 and 20 transfer power by mutual induction of electromagnetic energy over the air and through the body. The power supplied by the external power transmitter 21 may come from the detachable battery 24 or from a wall outlet, for example.

SUMMARY

The techniques of this disclosure generally relate to a digitally timed complementary metal oxide semiconductor (CMOS) rectifier for wireless power transfer in an implanted medical device.

An internal coil interface has a digital timing control circuit that adapts to load changes that occur when sending a digital communication signal to an external power transmitter. The digital timing control circuit controls an active state of an active rectifier circuit to rectify an AC voltage on the internal coil to produce a DC rectified voltage. Some embodiments described herein include an efficient voltage rectification circuit that employs cross coupled PMOS high-side (or NMOS low-side) field effect transistors (FETs) and actively driven low-side NMOS (or high-side PMOS) FETs. The low-side FETs are driven by the digital timing control circuit that actively adjusts for changes in rectification conditions. The digital timing control circuit also provides synchronization for a digital communication circuit that communicates a digital communication signal to an external power transmitter, which digital communication signal may facilitate closed loop power regulation, which enables a high signal to noise ratio (SNR) for the communication signal across operating conditions.

According to one aspect, a voltage rectification circuit for a medical device having an internal coil and internal circuitry is provided. The voltage rectification circuit includes a rectifier having actively driven first type transistors and cross-coupled second type transistors, a first type being one of N-type and P-type and a second type being an opposite one of the N-type and P-type, each low-side first-type transistor being configured with an first type diode; the rectifier configured to receive a time varying periodic voltage from the internal coil and to output a rectified received voltage, the actively driven first type transistors being further configured to receive an enable signal to cause the rectifier to switch between rectifier states, The voltage rectification circuit also includes a comparator configured to detect when the received voltage crosses a voltage threshold, the voltage threshold being sufficiently low to enable each actively driven first type transistor to conduct through the first type diode. The voltage rectification circuit also includes digital timing circuitry configured to: estimate windows of time for which the received time varying voltage can be expected to conduct through the first type diodes; and generate the enable signal to enable each actively driven first type transistor to conduct through a channel of the actively driven first type transistor while bypassing conduction through the first type diode.

According to this aspect, in some embodiments, the cross-coupled second type transistors and the actively driven first type transistors are referenced to ground and the enable signal is referenced to ground. In some embodiments, the voltage rectification circuit further includes a digital communication circuit configured to receive a synchronization signal from the digital timing circuitry and to provide a clock to modulate the load. In some embodiments, timing signals to modulate the load are only provided when a rectifier output is activated. In some embodiments, the first window of time is estimated based at least in part on a first load, and a second window of time is estimated based at least in part on a second load, the first window of time being subsequent to the first window of time. In some embodiments, the switching occurs without monitoring a rectifier input voltage when switching of load capacitances is enabled. In some embodiments, the rectifier is active when the actively driven first type transistors are enabled to conduct through respective actively driven first type transistor channels. In some embodiments, a duration of the first window of time is adjusted to maximize a time the AC coil voltage is above zero volts. In some embodiments, the enable signal is applied to a gate of an actively driven first type transistor. In some embodiments, the received voltage is applied between an actively driven first type transistor and a cross-coupled second type transistor.

In some embodiments, the diode is preferably a body diode associated with the construction of a MOS transistor. Those skilled in the art will realize that the diode may alternately be any component that conducts current in one direction with a forward bias voltage and blocks current in the opposing direction, such as any of: a diode, a Schottky diode, an NPN bipolar transistor, a PNP bipolar transistor, an N channel MOS transistor, a P channel MOS transistor, an N type JFET, or a P type JFET.

According to another aspect, a voltage rectification circuit for a medical device having an internal coil and internal circuitry is provided. The voltage rectification circuit includes a voltage rectifier comprising a complementary metal oxide semiconductor (CMOS) circuit having low-side first type MOS transistors and upper cross-coupled second type MOS transistors. A first type is one of N-type and P-type and a second type is an opposite one of the N-type and P-type. The voltage rectifier is configured to receive a time varying periodic voltage from the internal coil and to output a rectified received voltage. Each low-side first type MOS transistor is configured with a first type MOS body diode. The low-side first type MOS transistors are enabled by a timing signal to provide conduction through the low-side first type MOS transistors while bypassing conduction through the first type MOS body diode during a time window having a duration determined by voltage level crossings of the received voltage. The voltage rectification circuit also includes digital timing circuitry configured to provide the timing signal; the timing signal being based on the voltage level crossings.

According to this aspect, in some embodiments, the low-side first type MOS transistors are referenced to ground. In some embodiments, the duration of the time window increases when a load of the medical device increases and decreases when a load of the medical device decreases. In some embodiments, the digital timing circuitry is further configured to provide a synchronization signal to synchronize modulation of a load of a communication capacitance so that the communication capacitance is modulated only when a voltage on the communication capacitance is zero volts. In some embodiments, the load modulation encodes information to be transmitted from the internal circuitry via the internal coil to a power transmitter to enable closed loop regulation of power delivered by the power transmitter to the internal coil. In some embodiments, the voltage rectifier is active during the time window. In some embodiments, the duration of the time window is adjusted to minimize a time of a voltage level being below zero volts. In some embodiments, the digital timing circuitry causes load switching to occur without monitoring a rectifier input voltage when switching of a capacitive load is enabled. In some embodiments, the timing signal is applied to a gate of a low-side first type MOS transistor. In some embodiments, the received voltage is applied between a low-side first type MOS transistor and an upper cross-coupled second type MOS transistor.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

[Some embodiments described herein are related to a digitally timed complementary metal oxide semiconductor (CMOS) rectifier for wireless power transfer in an implanted medical device.

Figure 1:
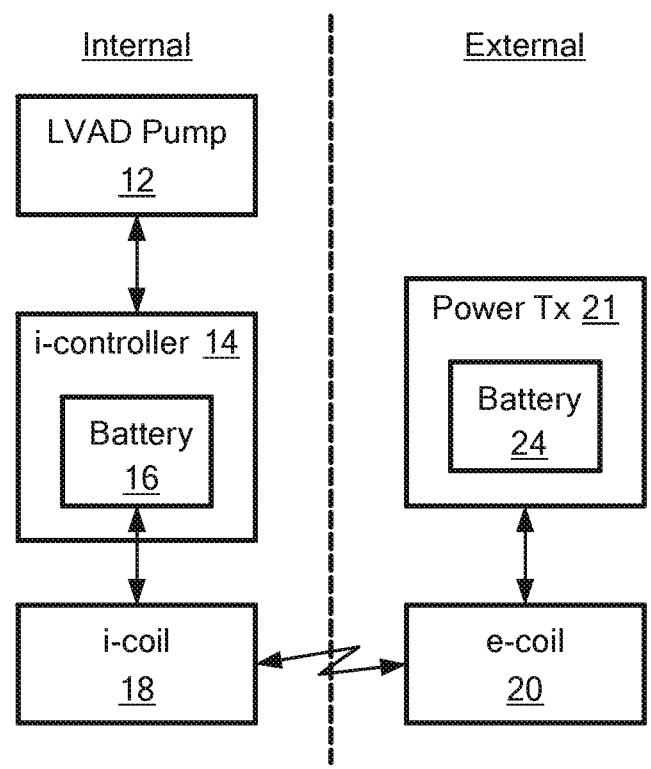
FIG. 1 is a block diagram of an implantable medical device.
Figure 2:
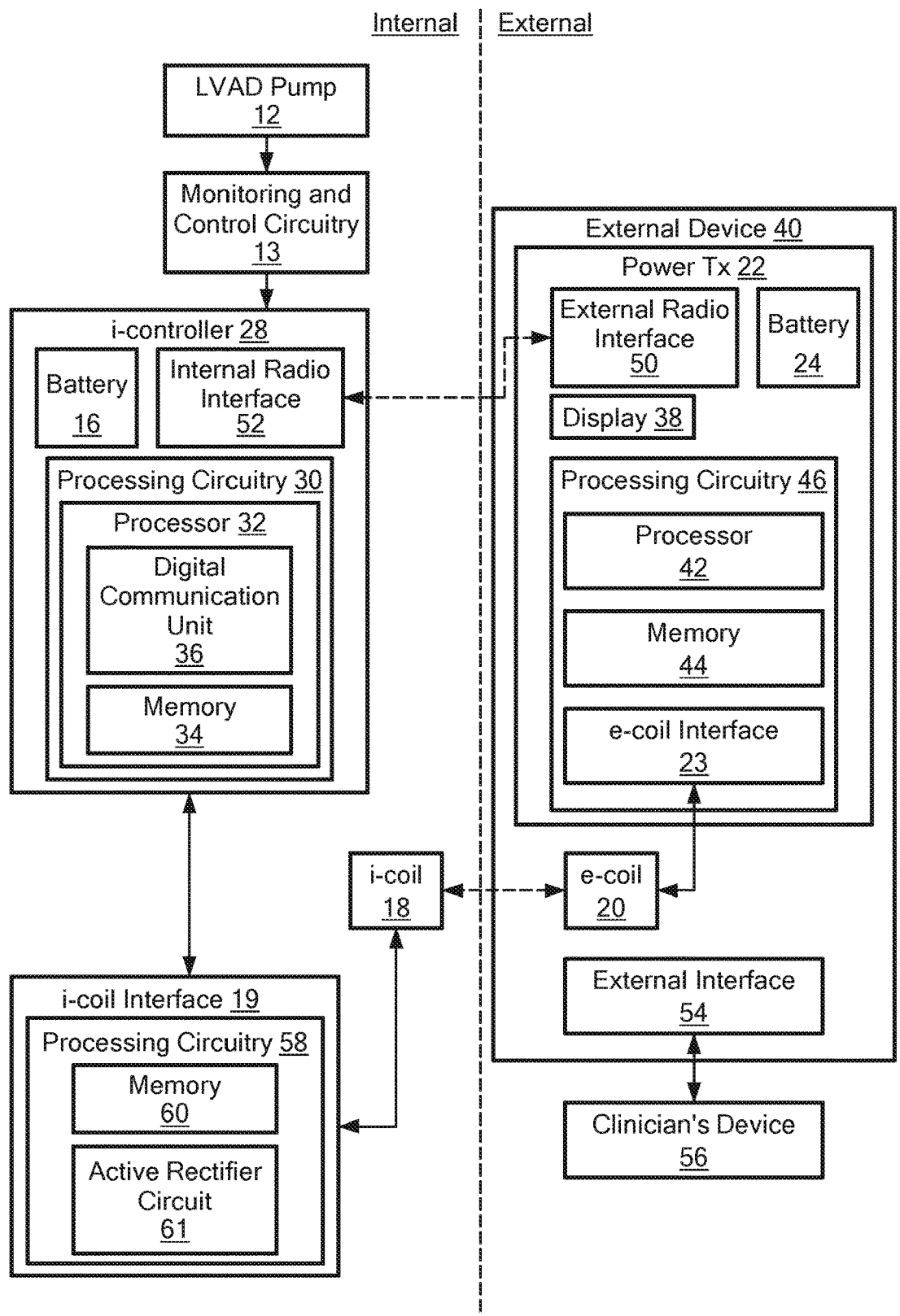
FIG. 2 is a block diagram of an embodiment of an LVAD system that implements a process of digitally timed complementary metal oxide semiconductor (CMOS) rectification.

Referring again to the drawing figures, FIG. 2 is a block diagram of one example configuration of an implanted medical device system 26 having external components such as an external power transmitter 22, and internal components such as an internal controller (i-controller) 28 configured to perform functions described herein. As used herein, the term "implanted medical device system 26" refers to the system that includes both the implanted/implantable components as well as external components described herein.

The i-controller 28 may have processing circuitry 30 which may include a processor 32 and an internal memory 34. The processor 32 may be configured to execute computer instructions stored in the internal memory 34. Those instructions may include instructions to cause the processor to perform some of the processes described in more detail below. The processor 32 may therefore implement a digital communication unit 36 to provide digital communication signals to be transmitted to the external power transmitter A message or result from the digital communication unit 36 may be transferred from the i-controller 28 to an external display 38 of an external device 40, which may include a processor 42 and a memory 44 within processing circuitry 46, the external power transmitter 22 and the detachable battery 24, as well as the e-coil 20 in some embodiments. The memory 44 may be configured to store computer instructions to be executed by the processor 42. The external display 38 may be configured to display information received from the i-controller 28.

Electrical communication of signals and power between the internal components of i-controller 28 may be via communication busses and individual electrical conductors not shown in FIG. 2. For example, a multi-conductor address bus and data bus may connect processor 32 with internal memory 34. In some embodiments, an i-coil interface 19 associated with i-coil 18 may be included in the set of internal components making up the implanted medical device system 26. One purpose of i-coil interface 19 may be to modulate the alternating current applied to the i-coil 18 with signals from the i-controller 28 to be transmitted from the i-coil 18 to the e-coil 20 and/or to demodulate signals to be received by the i-coil 18 from the e-coil 20. In some embodiments, a purpose of the i-coil interface 19 is to provide conversion between the alternating current (AC) of the i-coil 18 and direct current (DC) to charge the battery 16.

The i-coil interface 19 may include processing circuitry 58 which includes a memory 60 to perform the functions and procedures of an active rectifier circuit 61. The active rectifier circuit 61 is responsive to a time-varying, cyclic voltage on the i-coil 18 and converts this time-varying voltage to a DC voltage.

The power supplied to the i-coil 18 may be adjusted by varying the AC electrical current in the e-coil 20. Some or all functions of the i-coil interface 19 may be included in the i-controller 28 and/or the i-coil 18. In some embodiments, the i-coil 18 and/or i-coil interface 19 may be internal to or considered part of the internal controller 28. Similarly, electrical communication of signals and power between the internal components of external device may be by communication busses and individual electrical conductors not shown in FIG. 2. For example, a multi-conductor address bus and data bus may connect processor 42 with memory 44.

In some embodiments, an e-coil interface 23 associated with e-coil 20 may be included in the set of external components making up the implanted medical device system 26. The e-coil interface 23 may include a TETS interface configured to demodulate information signals from the processing circuitry 30 transmitted from the i-coil 18 to the e-coil 20. The e-coil interface 23 may also be configured to couple power from the external power transmitter 22 to the e-coil 20. In some embodiments, the e-coil interface 23 may be two distinct units, one unit for demodulation of signals from the i-controller that are uploaded via the coils 18 and 20, and one unit for coupling power from the external power transmitter 22 to the e-coil 20. In some embodiments, the i-controller 28 may upload information to the external power transmitter 22 via the coils 18 and 20, but the power transmitter does not download information to the i-controller 28 via the coils 18 and 20.

In some embodiments, the internal components of the implanted medical device system 26 may include monitoring and control circuitry 13. A purpose of monitoring and control circuitry 13 may include monitoring speed and temperature, for example, of the LVAD pump 12. Another purpose of the monitoring and control circuitry 13 may include controlling the speed of the LVAD pump 12. In some embodiments, some or all of the monitoring and control circuitry 13 may be incorporated into the LVAD pump 12 and/or the i-controller 28. In some embodiments, some or all of the functions performed by the monitoring and control circuitry 13 may be performed by the processing circuitry 30. Thus, in some embodiments, the monitoring and control circuitry 13 may include one or more temperature sensors embedded in the LVAD pump 12. Information obtained from and/or about the LVAD pump 12, such as speed and temperature, may be sent to the external device 40 to be displayed by external display 38.

The various internal components making up the LVAD system may be grouped into one or more separate housings. Similarly, the various external components making up the LVAD system may be grouped into one or more separate housings. Further, some of the components shown and described as being internal to the i-controller 28 may be instead, external to i-controller 28 in some embodiments. Similarly, some of the components shown and described as being internal to the external device 40 may be instead, external to external device 40, in some embodiments. Note further that some of the functions performed by processor 32 may be performed instead by processor 42.

Note that transfer of information from the external device 40 to the internal memory 34, and vice versa, may be by wireless radio frequency (RF) transmission (over the air and through the body when the i-controller 28 is implanted). Accordingly, in some embodiments, the external device 40 includes an external radio interface 50 and the i-controller 28 includes an internal radio interface 52. In some embodiments, the external radio interface 50 and the internal radio interface 52 are RF transceivers having both an RF receiver for receiving information wirelessly and an RF transmitter for transmitting information wirelessly. Such RF transceivers may be Bluetooth and/or Wi-Fi compliant, for example. In some embodiments, the RF receiver and RF transmitter within the external device 40 or within the i-controller 28 are integrated into one unit, whereas in some embodiments, they could be physically separate units.

Also, information may be communicated to the i-controller 28 from the external power transmitter 22 via the coils 18 and 20, by modulating a parameter of power transmission, such as modulating the frequency of the transmitted power, or by modulating a parameter of the i-coil interface 19, for example, by modulating a tuning capacitance of the i-coil interface 19 or by modulating the load level of the i-controller and/or the i-coil interface 19.

The external device 40 could be a patient's external device that has an external interface 54 which provides an interface between the external device 40 and a clinician's device 56. The clinician's device might, for example, have a USB port and interface 54 might include a USB port, so that a USB cable may connect the two ports. The clinician's device 56 may read data from the external device 40 and write information and control signaling to the external device 40, in some embodiments. In the alternative to a wireline connection, the interface 54 could include or be a radio interface.

Figure 3:
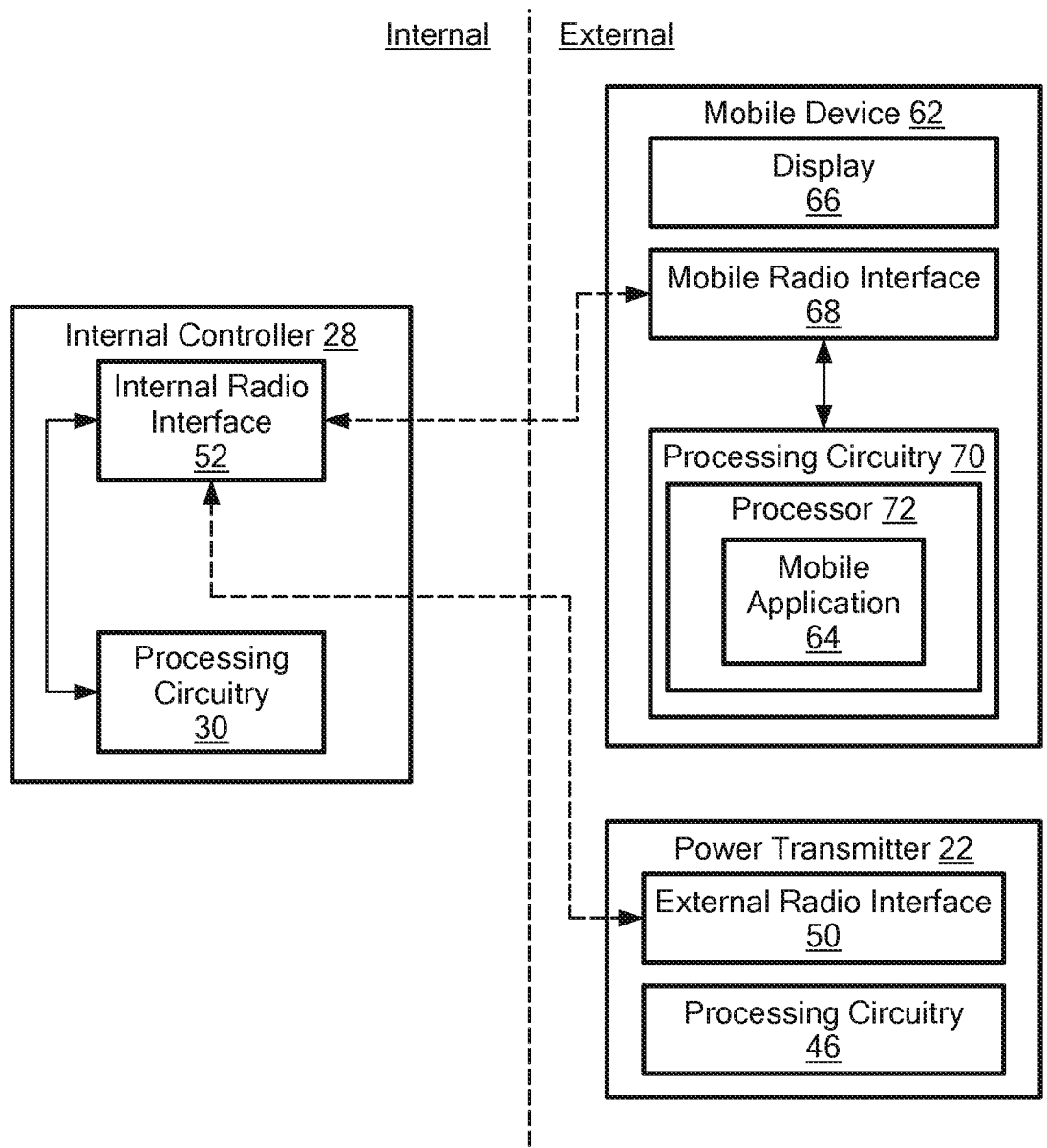
FIG. 3 is a block diagram of an embodiment that includes a mobile device.

FIG. 3 is a block diagram of an implanted medical device system 26 that includes a mobile device 62 with a mobile application 64 in wireless communication with the i-controller 28. The mobile device 62 may be a mobile phone or other mobile digital device that can process information and communicate wirelessly with the i-controller. Accordingly, the mobile device 62 has a display 66, a mobile radio interface 68, processing circuitry 70 and a processor 72 which runs the mobile application 64. The radio interfaces 50, 52 and 68 may be Bluetooth Low Energy compatible radio interfaces, and the i-controller 28 may be a peripheral device responsible for advertising, while the mobile device 62 and the external power transmitter 22 may operate as master or central devices responsible for scanning and issuing connection requests.

Communication from the i-controller 28 to the external power transmitter 22 enables display on the external display 38 of implanted device information such as pump data and alarm indications. The i-controller 28 may exchange, via the radio interfaces 50 and 52, diagnostic and log file data with the external power transmitter 22. The i-controller 28 may receive programming commands from an external device such as the clinician's device 56 or mobile device 62. Further, communication from the i-controller 28 to the mobile device 62, via the radio interfaces 52 and 68, enables remote monitoring in cases where the mobile device 62 is connected to the Internet, and enables the display 66 to display information about the state of the implanted portion of the implanted medical device system 26 such as, for example, remaining battery runtime. In some embodiments, the internal radio interface 52 may only communicate with the external radio interface 50 and the mobile radio interface 68 one at a time. In some embodiments, when the i-controller 28 is not engaged in a communication session with an external device, such as external power transmitter 22 or mobile device 62, the i-controller 28 may advertise continually to enable rapid reestablishment of the wireless connection between the i-controller 28 and the external power transmitter 22 or mobile device 62. Conversely, either one or both of the external power transmitter 22 or mobile device 62 may scan for such advertisements.

Figure 4:
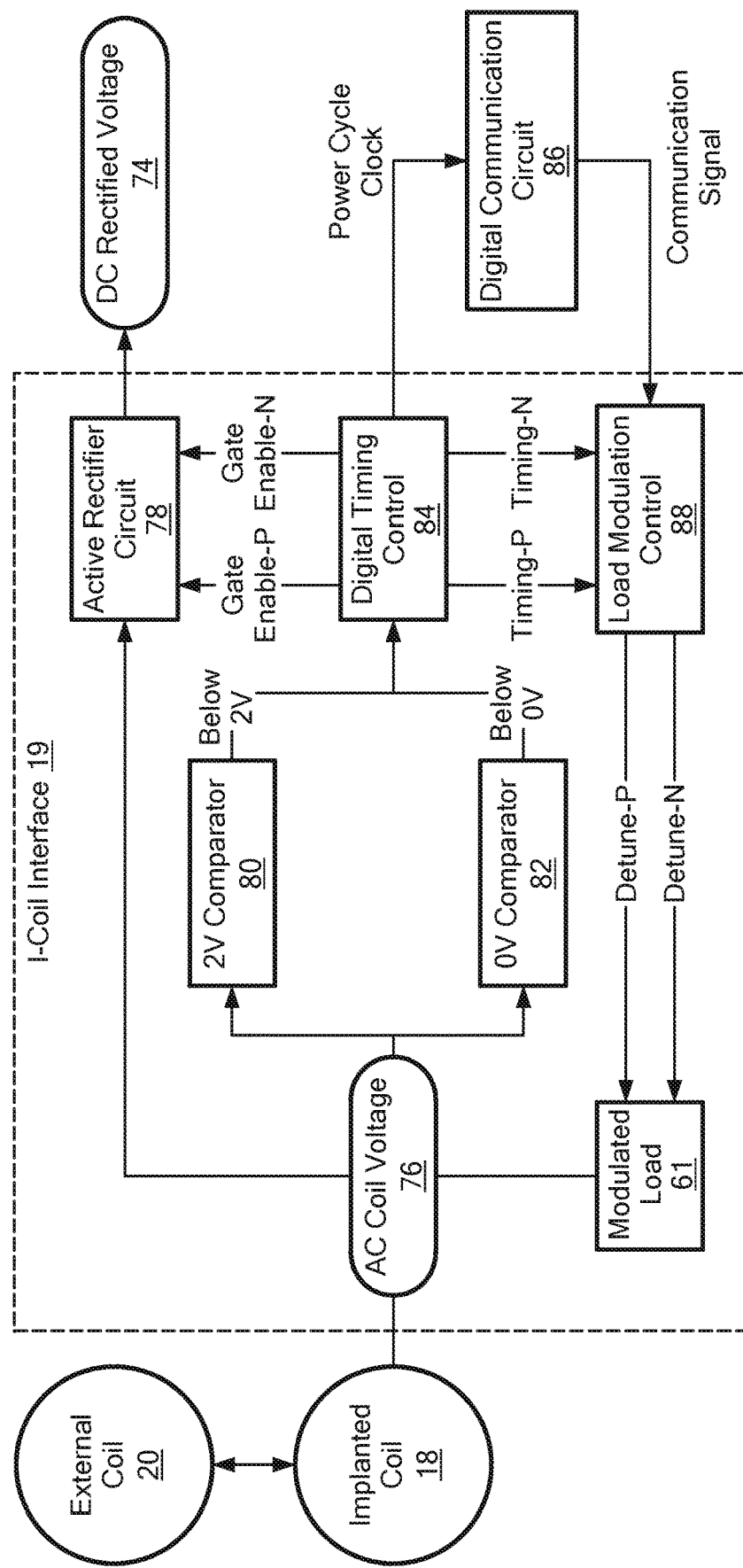
FIG. 4 is a block diagram of an internal coil interface configured according to principles set forth herein.

FIG. 4 is a block diagram of circuitry configured to provide a DC rectified voltage 74 which is generated from a power signal inductively transmitted from the e-coil 20 to the i-coil 18. This induces in the i-coil 18 an AC coil voltage 76. The AC coil voltage 76 is received by the active rectifier circuit 61, which rectifies the AC coil voltage 76 to produce the DC rectified voltage 74. The AC coil voltage 76 is also sent to a first voltage comparator 80 and a second voltage comparator 82. The first voltage comparator 80 compares the AC coil voltage 76 to a first threshold to produce a first compare signal. The second voltage comparator 82 compares the AC coil voltage 76 to a second threshold lower than the first threshold to produce a second compare signal. For example, the first threshold may be 2 volts and the second threshold may be 0 volts. In some embodiments, the first and second thresholds are fixed and do not change over time. The first and second thresholds may be determined based on characteristics of transistor circuits included in the active rectifier circuit 61.

In the example of FIG. 4, when the AC coil voltage 76 falls below 2 volts, a signal indicating this fact is sent from the first voltage comparator 80 to a digital timing control circuit 84. Similarly, when the AC voltage falls below 0 volts, a signal indicating this fact is sent from the second voltage comparator 82 to the digital timing control circuit 84. The signals enable the digital timing control circuit 84 to generate a gate enable-P signal and a gate enable-N signal. The gate enable-P signal and the gate enable-N signal control rectification of the AC coil voltage 76 by the active rectifier circuit 61. The digital timing control circuit 84 may also generate a clock to control timing of a digital communication circuit 86. The digital communication circuit 86 generates communication signals to a load modulation control circuit 88, and may be implemented as digital communication unit 36. The communication signals sent to the load modulation control circuit 88 may include information to be transmitted from the i-controller 28 to the external power transmitter 22 via the i-coil 18 and the e-coil 20. The load modulation control circuit 88 generates two load modulation signals: a detune-P enable signal and a detune-N enable signal. These signals are used to modulate a load of the modulated load circuit 90. Modulation of the modulated load circuit 90 causes the AC coil voltage 76 to vary. These variations are detected by the external power transmitter 22.

In some embodiments, the components numbered 61, 74, 76, 80-84, 88 and 90 may be implemented within the i-coil interface 19 and/or the i-controller 28. The digital communication circuit 86 may be implemented within the i-controller 28 as digital communication unit 36.

A purpose of the i-coil interface 19 is to determine the appropriate timing for connecting the i-coil 18 to the load presented by the implanted circuitry in order to pass energy to such load. The appropriate time to make this connection is when the voltage on the i-coil 18 is equal to the voltage on the implanted circuitry, including the i-controller 28. This timing is not directly measured, but rather is estimated. The signal from the first voltage comparator 80 signals when the AC coil voltage 76 is approaching the second threshold.

Figure 5:
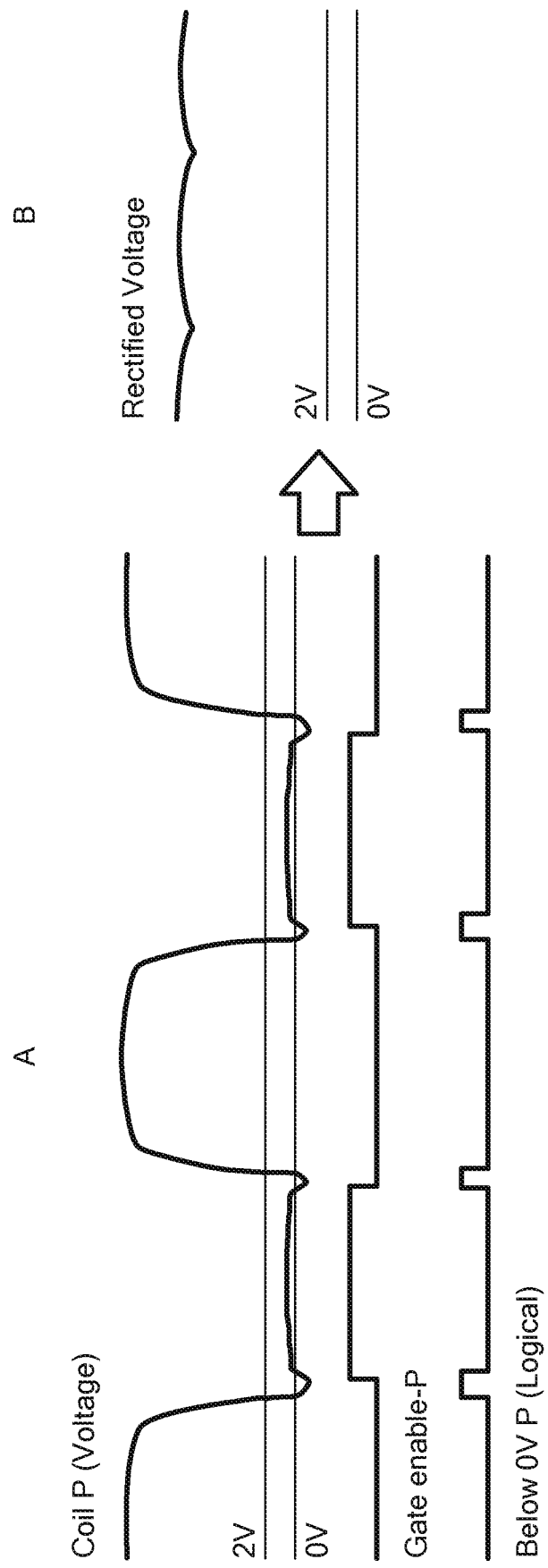
FIG. 5 is a timing diagram showing timing of the voltage on a coil terminal, examples of thresholds, and an enable signal.

FIG. 5 is a timing diagram that shows the timing relationships between the AC coil voltage 76 and the gate enable-P signal. For the example of FIG. 5, the first threshold is 2 volts and the second threshold is zero volts. The signal at the top of side A of FIG. 5 is the AC coil voltage on a P terminal of the i-coil 18. In a first cycle, the AC coil voltage on the P terminal of the i-coil 18 falls below the 2 volt threshold and then falls below the 0 volt threshold for a short period of time, resulting in the below 0V logic signal at the bottom of side A of FIG. 5. In the timing example of FIG. 5, at about the time that the AC coil voltage on the P-terminal of the i-coil 18 crosses the 0 volt threshold, the gate enable-P signal shown on side A of FIG. 5, transitions from low to high. Note that a similar timing relationship may exist for the AC coil voltage on the N terminal of the i-coil 18. The P terminal AC coil voltage may be 180 degrees out of phase with the N terminal AC coil voltage. Similarly, the gate enable-P signal may be 180 degrees out of phase with the gate enable-N signal. Side B of FIG. 5 shows the DC rectified voltage 74 desirably having ripple that is smaller than a maximum tolerable ripple.

The duration of time during which a gate enable signal is at zero volts defines a duration of time during which the enable signal is active (high, in FIG. 5). The duration of time during which the enable signal is active is referred to herein as the active window. During the active window, the rectifier may be said to be active.

Figure 6:
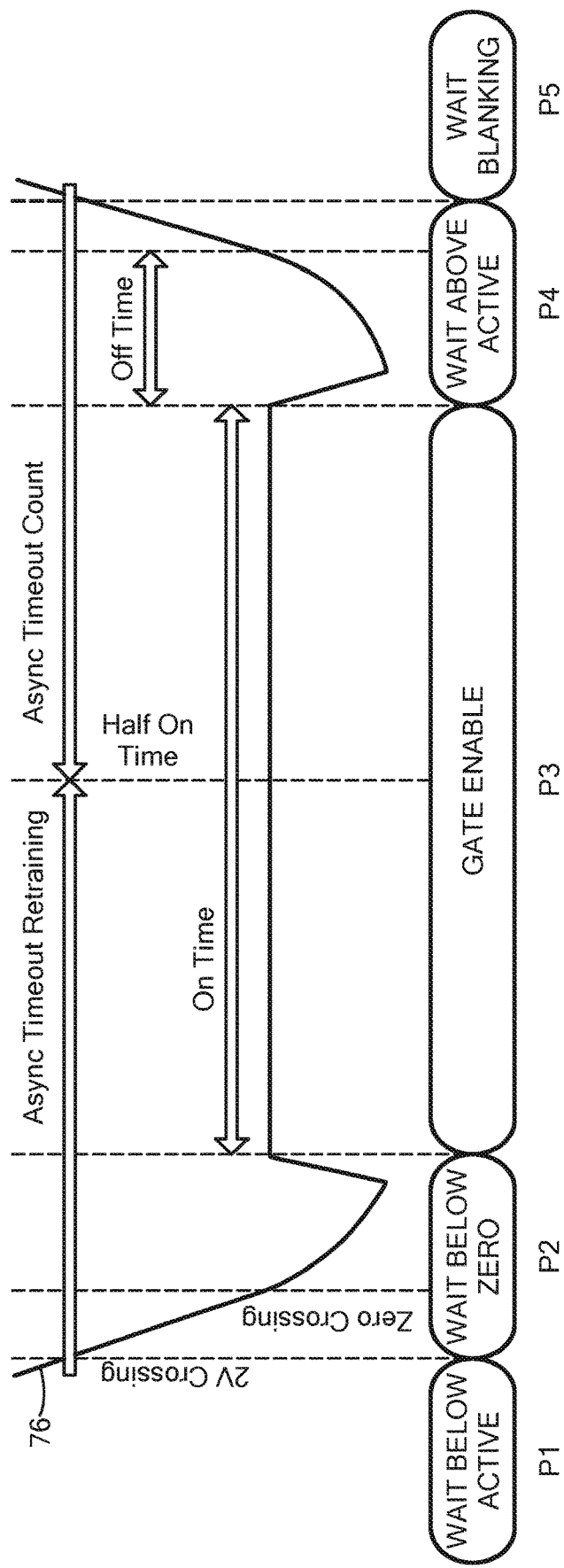
FIG. 6 is a timing diagram of states of a digital timing control circuit.

FIG. 6 shows a more detailed example of the transitions of the AC coil voltage 76 above and below the 2 and 0 volt thresholds, and the timing of the gate enable signal (gate enable-P or gate enable-N). In a first wait below active state during time period P1, the AC coil voltage 76 is above the 2 volt threshold (also referred to as the 2 volt level). When the AC coil voltage 76 crosses the 2 volt threshold the digital timing control circuit 84 transitions to a wait below zero state during time period P2. During the wait below zero state, the AC coil voltage 76 dips below the 0 volt threshold (also referred to as the 0 volt level). When the AC coil voltage 76 returns to 0 volts, the digital timing control circuit 84 enters the gate enable state during the time period P3. During this time period, the gate enable signal is active. The on-time arrow extends from the beginning of the gate enable state to the end of the gate enable state. This is the window of time that the active rectifier circuit 61 is said to be active. In the middle of the gate enable time period P3, a clock pulse is sent to the digital communication circuit 86 to properly time switching of capacitances of the modulated load circuit 90. At the end of the half cycle, the AC coil voltage 76 falls below 0 volts, marking the end of the gate enable time period P3 and the start of a wait above active state during time period P4. During the wait above active state, the AC coil voltage 76 rises and reaches the 0 volt level. This time period marks the off time of the active rectifier circuit 61. During the wait above active state, the AC coil voltage 76 continues to rise and reaches the 2 volt level, marking the end of the wait above active state.

Figure 7:
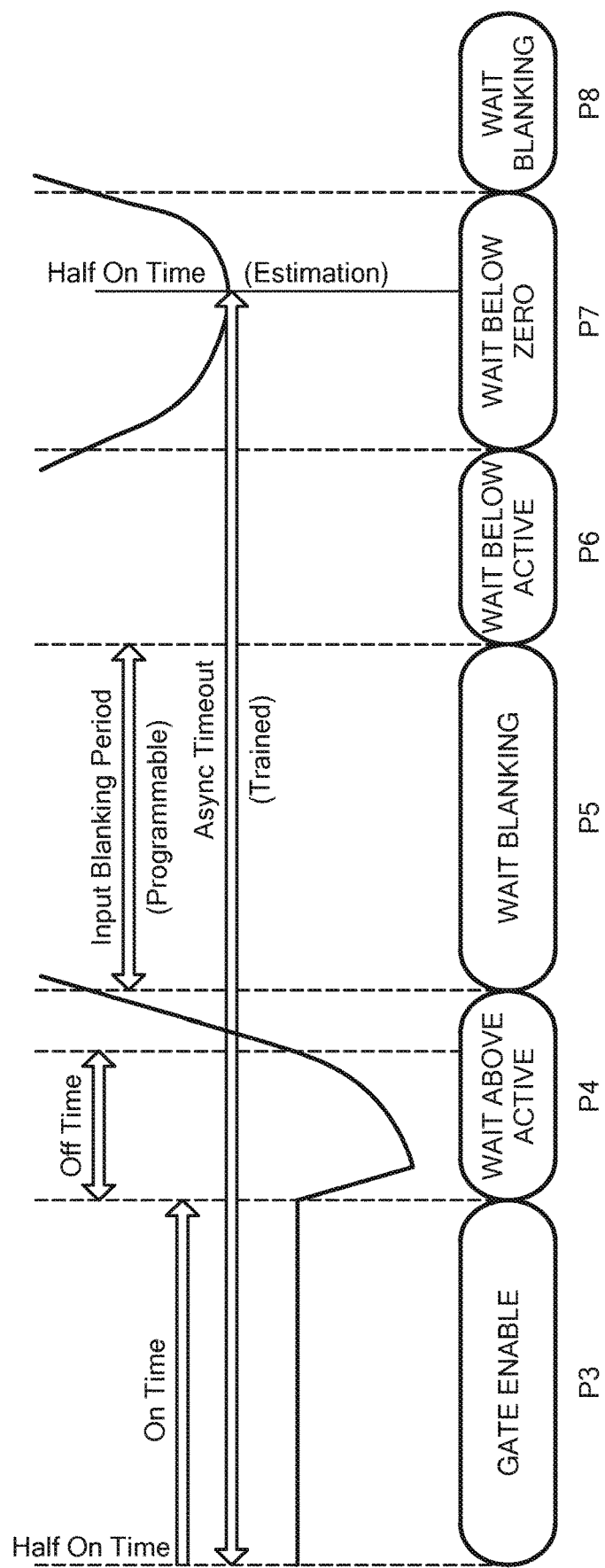
FIG. 7 is a continuation of the timing diagram of FIG. 6.

A count is maintained to track the period of oscillations of the AC coil voltage 76. This count is adjusted so that it starts and ends in the middle of the active window (in the middle of period P3). A normal cycle is one where the AC coil voltage 76 crosses zero and back in an expected window. If two consecutive normal cycles occur, the count is adjusted. If the AC coil voltage 76 does not cross zero, the count is not adjusted. When the count rolls over, indicating the middle of the active window, a clock pulse is sent to the digital communication circuit 86 to properly time switching of capacitances of the modulated load circuit 90. The gate enable window is of a duration that may be optimized to maintain a 40 MHz count of 2, for example, for "Off Count, where Off Count refers to an off time of a window which follows an off time window. Such window may be useful to ensure that the gate of the lower transistor is not on at an end of a power cycle. At least one cycle of "below zero" should be observed for the timer counts to be maintained." FIG. 7 shows a continuation in time of FIG. 6. At the end of the wait above active period P4, during the wait blanking period P5, the digital timing control circuit 84 will enter an input blanking period of programmable duration. The input blanking window is configured to remove sensitivity to timing signals when a 2 volt crossing is invalid or unexpected. At the end of the input blanking period P5, the digital timing control circuit 84 transitions to the wait below active state during period P6. The wait below active period P6 ends when the AC coil voltage 76 once again crosses the two volt level while decreasing. Then, the digital timing control circuit 84 transitions to the wait below zero state during time period P7. In the example, of FIG. 7, instead of returning to and dipping below zero, as it did before during period P2, the AC coil voltage 76 rises again and crosses the 2 volt level. This ends the wait below zero period P7 and begins another wait blanking period P8 similar to period P5. The decision to transition to the wait blanking state from the wait below zero state during period P7, is based on an asynchronous timer that starts at the middle of the gate enable period P3 and ends at a time estimated to be in the middle of the next low half cycle of the AC coil voltage 76 after the half cycle encompassing period P3. An asynchronous timeout may be derived from timer that estimates the average period of the power cycle, starting from the middle of the GateEnable/OnTime window. If the timeout occurs before the voltage goes below zero, and the next GateEnable state is entered, a clock pulse is sent to the communications circuit. This feature may be useful for maintenance communications timing.

The clock from the digital timing control circuit 84 is used to time transmission of symbols by the digital communication circuit 86 accurately without a dedicated oscillator providing the clock. This clock is provided during the active window. By providing the carrier clock pulse in the middle of the active window (in the gate enable state), the load modulation capacitances are switched in and out when the voltage is zero. This minimizes noise induced by switching and contributes to a high signal to noise ratio (SNR) of a digital communication signal to be transmitted via the i-coil 18 and the e-coil 20 to the external power transmitter 22. If switching is not performed at the proper time, switching noise can degrade signal integrity. Switching the capacitive load into and out of the modulated load circuit may produce a digital communication signal that is visible via the coupling between the i-coil 18 and the e-coil to the external power transmitter 22. This method of communication may be used to facilitate closed loop power regulation.

Figure 8:
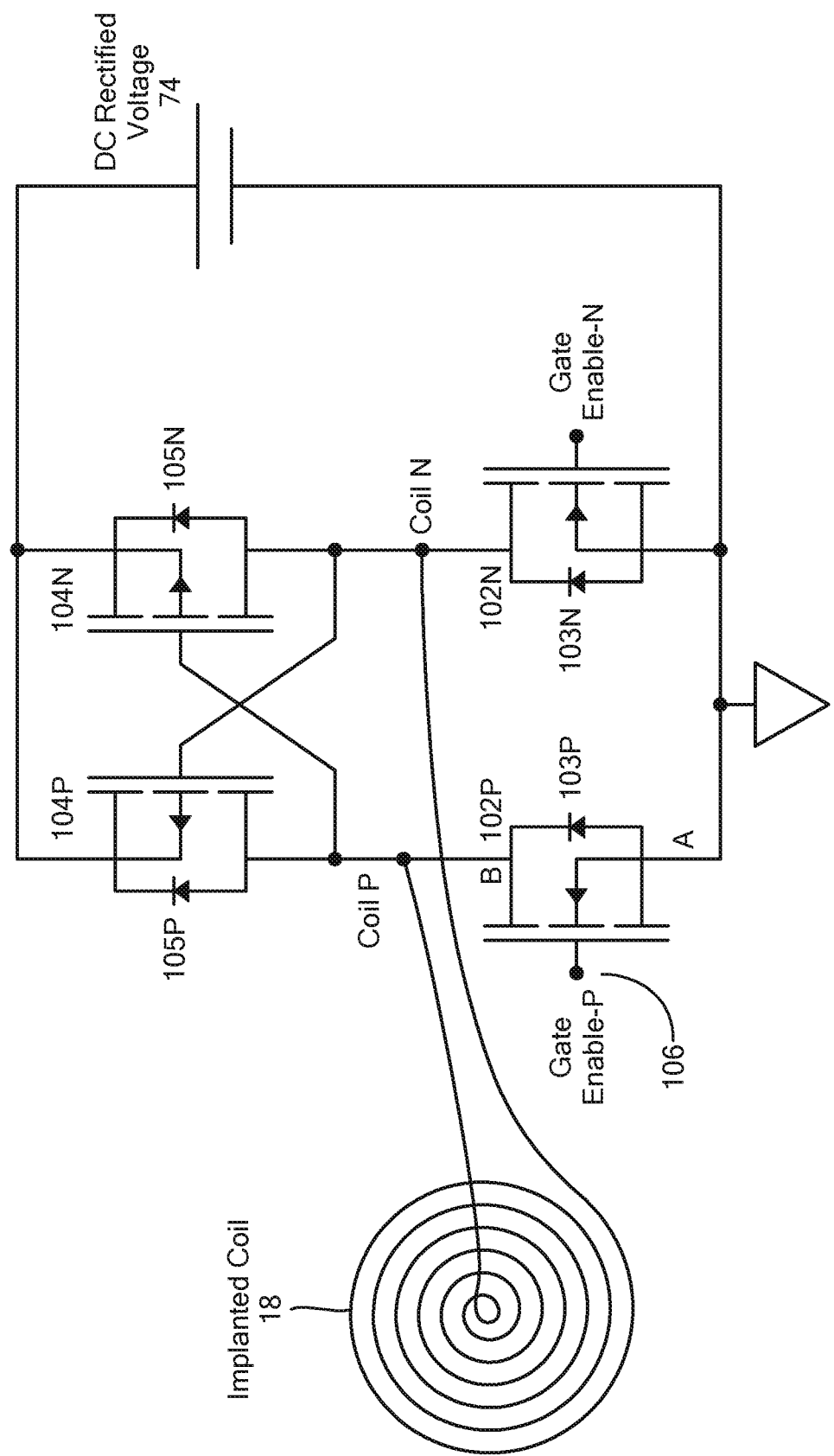
FIG. 8 is schematic of an active rectifier circuit responsive to enable signals.

FIG. 8 illustrates the i-coil 18 in electrical communication with an embodiment of the active rectifier circuit 61 electrically connected to the i-coil 18 and configured to receive the gate enable-P and gate enable-N signals from the digital timing control circuit 84. One terminal of the i-coil 18 is electrically connected as shown in FIG. 8 to a P-side of the active rectifier circuit 61 and another terminal of the i-coil 18 is electrically connected to an N-side of the active rectifier circuit 61. The P-side of the active rectifier circuit 61 has a first lower transistor 102P and a body diode 103P.

A transistor enables regulation of current through the body of the transistor from terminal A to terminal B (or vice versa). The current is regulated by varying the voltage on the gate 106 of the transistor 102P. The gate enable signal applied to the gate 106 causes electrical current through the transistor 102P to increase or decrease, and may completely turn off electrical current through the transistor 102P. During the active window, the body diode 103P is reverse biased and electrical current flows through the transistor 102P. At other times, the body diode 103P is forward biased and electrical current does not flow through the transistor 102P, but rather, flows through the body diode 103P.

The N-side of the active rectifier circuit 61 has the second lower transistor 102N and a body diode 103N. The transistor 102P receives the gate enable-P signal from digital timing control circuit 84. The transistor 102N receives the gate enable-N signal from the digital timing control circuit 84. Both lower transistors 102P and 102N may be NMOS transistors or both may be PMOS transistors. When the lower transistors 102P and 102N are NMOS transistors, the upper cross-coupled transistors 104P and 104N are PMOS transistors. The upper cross-coupled transistors 104P and 104N are each in a sub-circuit that includes body diode 105P and 105N, respectively. Conversely, when the lower transistors 102P and 102N are PMOS transistors, the upper cross-coupled transistors 104P and 104N are NMOS transistors. Herein, the active rectifier circuit 61 is discussed for the lower transistors 102P and 102N being NMOS transistors, but operation of the active rectifier circuit 61 is equivalent when the lower transistors are PMOS transistors. Similarly, statements made herein concerning the lower transistor 102P and body diode 103P are true for the lower transistor 102N and body diode 103N.

In the alternative to cross coupled high side FETS and actively driven low-side FETS, some embodiments have cross-coupled low side FETS and actively driven high side FETS. Operation of these embodiments mirrors operation of the embodiments having cross-coupled high side FETS and actively driven low side FETS. The same concepts described here for driving NMOS FETS can be employed to drive the PMOS FETS, instead. For example, the PMOS FETS could be driven by a complementary circuit that references a positive supply voltage, and include timing related to when the diode conducts and the AC coil voltage goes above the positive supply voltage. In some embodiments, the PMOS FETS could be driven by a signal from a digital timing control circuit, since conduction through a parallel diode on the PMOS to the positive voltage supply could be concurrent with conduction thru the parallel diode on an opposing NMOS FET. Also, the theory of operation described above and below may be implemented by using FETS or bipolar transistors or other types of transistors that exhibit a P-type or N-type characteristic. Thus, in an alternative embodiment, high side PMOS FETS and the low side NMOS FETS can both be actively driven, rather than having one of the low side and high side being cross-coupled. In some of these embodiments, the conduction through the diode parallel to the high side PMOS FET on one side of the coil is concurrent with the low side NMOS FET on the opposite side of the coil. Due to this concurrence, sensing on both the high side and low side of the circuit would not be used to generate drive signals for the high and low side FETS.

During an active window (when the AC coil voltage 76 is low), the gate enable-P signal is active and the lower transistor 102P conducts current rather than the body diode 103P. Similarly, during another active window, the gate enable-N signal is active and the lower transistor 102N conducts current rather than the body diode 103N.

The duration of the active window is based at least in part on a load of the implanted circuitry. A large system load may generally result in a longer active window and a small system load may generally result in a shorter active window. The small load changes from communication modulation are accounted for by having separate windows tracking the different stages of modulation (load is switched in, load is switched out, etc.). Tracking is performed by monitoring the 'below 2V' and 'below 0V' signals produced by the voltage comparators. In each tracking window, the active window is adjusted to minimize or eliminate the 'below 0V' signal. The 'below 2V' signal is used to start the sequence leading to the active window. Such a sequence may occur over one period of the power cycle. The power cycle may include: WaitBelowActive(2V), WaitBelowZero(0V), GateEnable, WaitAboveActive(2V) and WaitBlanking. The steps may sequence in that order, with the exception being that WaitBelowZero can also transition to WaitBlanking if the 2V level is crossed.

It is desirable to minimize conduction through the body diode 103P of the transistor 102P which would call for a longer active window. However, the window should not be longer than the diode conduction time of the body diode 103P. Therefore, when the active window is in a steady state condition, the active window will modulate between two values so that the "below 0V" signal is observed occasionally. The logic for this behavior is as follows: if the "below 0V" signal is observed, increase the active window duration, else, decrease the active window duration. Diode conduction is detected as the 'below 0V' signal. When conducting through the body diode of the NMOS device, the coil voltage will be below 0V. The digital timing circuitry therefore attempts to minimize body diode conduction through the feedback of the 'below 0V' signal.

Actively driving the low-side NMOS devices reduces conduction losses. Using digital timing rather than monitoring an analog voltage enables use of low resistance rectifier transistors, 102N, 102P, 104N and 104P, thereby further reducing conduction losses by eliminating a need to monitor the voltage when the switches are enabled. Also, the digital timing control circuit 84 adapts to changes in timing caused by load modulation to communicate a digital signal by tracking multiple timing windows independently, corresponding to dynamics introduced by a communication channel. The active rectifier circuit 61 described above provides timing for the communication channel to improve signal integrity over a wide variety of loads and power transfer coupling. Digital control of the low-side NMOS FETS may eliminate the need for low latency comparators by enabling delay and latency to be automatically compensated. Some embodiments eliminate the need for gate drivers. Using cross coupled PMOS high side rectifier transistors and actively driven low side transistors that are ground referenced allows the controlling gate enable signals to be ground referenced, thereby eliminating the need for level shifting of drive signals to the rectifier output voltage.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media and memory may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope of the invention, which is limited only by the following claims.

What is claimed is:

1. A voltage rectification circuit for a medical device having an internal coil and internal circuitry, the voltage rectification circuit comprising:
   a rectifier having actively driven low-side first type transistors and cross-coupled second type transistors, a first type being one of N-type and P-type and a second type being an opposite one of the N-type and P-type, each low-side first-type transistor being configured with a first type diode; the rectifier configured to receive a time varying periodic voltage from the internal coil and to output a rectified received voltage, the actively driven first type transistors being further configured to receive an enable signal to cause the rectifier to switch between rectifier states;
   a comparator configured to detect when the received time varying voltage crosses a voltage threshold, the voltage threshold being sufficiently low to enable each actively driven first type transistor to conduct through the first type diode;
   digital timing circuitry configured to:
      estimate windows of time for which the received time varying voltage can be expected to conduct through the first type diodes; and
   generate the enable signal to enable each actively driven first type transistor to conduct through a channel of the actively driven first type transistor while bypassing conduction through the first type diode.

2. The voltage rectification circuit of claim 1, wherein the cross-coupled second type transistors and the actively driven first type transistors are referenced to ground and the enable signal is referenced to ground.

3. The voltage rectification circuit of claim 1, further comprising a digital communication circuit configured to receive a synchronization signal from the digital timing circuitry and to provide a clock to modulate a load.

4. The voltage rectification circuit of claim 3, wherein timing signals to modulate the load are only provided when a rectifier output is activated.

5. The voltage rectification circuit of claim 1, wherein the first window of time is estimated based at least in part on a first load, and a second window of time is estimated based at least in part on a second load, the first window of time being subsequent to the first window of time.

6. The voltage rectification circuit of claim 5, wherein the rectifier switching occurs without monitoring a rectifier input voltage when switching of load capacitances is enabled.

7. The voltage rectification circuit of claim 1, wherein the rectifier is active when the actively driven first type transistors are enabled to conduct through respective actively driven first type transistor channels.

8. The voltage rectification circuit of claim 1, wherein a duration of a first window of time is adjusted to maximize a time that an AC coil voltage is above zero volts.

9. The voltage rectification circuit of claim 1, wherein the enable signal is applied to a gate of an actively driven first type transistor.

10. The voltage rectification circuit of claim 1, wherein the received time varying voltage is applied between an actively driven first type transistor and a cross-coupled second type transistor.

11. A voltage rectification circuit for a medical device having an internal coil and internal circuitry, the voltage rectification circuit comprising:
- a voltage rectifier comprising a complementary metal oxide semiconductor (CMOS) circuit having low-side first type MOS transistors and upper cross-coupled second type MOS transistors, a first type being one of N-type and P-type and a second type being an opposite one of the N-type and P-type, the voltage rectifier configured to receive a time varying periodic voltage from the internal coil and to output a rectified received voltage, each low-side first type MOS transistor being configured with a first type MOS body diode, the low-side first type MOS transistors being enabled by a timing signal to provide conduction through the low-side first type MOS transistors while bypassing conduction through the first type MOS body diode during a time window having a duration determined by voltage level crossings of the received time varying voltage, a voltage level being a threshold voltage; and
- digital timing circuitry configured to provide the timing signal; the timing signal being based on the voltage level crossings.

12. The voltage rectification circuit of claim 11, wherein the low-side first type MOS transistors are referenced to ground.

13. The voltage rectification circuit of claim 11, wherein the duration of the time window increases when a load of the medical device increases and decreases when a load of the medical device decreases.

14. The voltage rectification circuit of claim 11, wherein the digital timing circuitry is further configured to provide a synchronization signal to synchronize modulation of a load of a communication capacitance so that the communication capacitance is modulated only when a voltage on the communication capacitance is zero volts.

15. The voltage rectification circuit of claim 14, wherein the load modulation encodes information to be transmitted from the internal circuitry via the internal coil to a power transmitter to enable closed loop regulation of power delivered by the power transmitter to the internal coil.

16. The voltage rectification circuit of claim 11, wherein the voltage rectifier is active during the time window.

17. The voltage rectification circuit of claim 11, wherein the duration of the time window is adjusted to minimize a time of a voltage level being below zero volts.

18. The voltage rectification circuit of claim 11, wherein the digital timing circuitry causes load switching to occur without monitoring a rectifier input voltage when switching of a capacitive load is enabled.

19. The voltage rectification circuit of claim 11, wherein the timing signal is applied to a gate of a low-side first type MOS transistor.

20. The voltage rectification circuit of claim 11, wherein the received time varying voltage is applied between a low-side first type MOS transistor and an upper cross-coupled second type MOS transistor.

* * * * *